United States Patent [19]

Heinrich

[11] Patent Number: 5,608,574
[45] Date of Patent: Mar. 4, 1997

[54] SURGICAL DRAPE FOR AN OPERATION MICROSCOPE

[75] Inventor: Lutz Heinrich, White Plains, N.Y.

[73] Assignee: Carl Zeiss, Inc., Thornwood, N.Y.

[21] Appl. No.: 577,231

[22] Filed: Dec. 22, 1995

Related U.S. Application Data

[63] Continuation-in-part of Ser. No. 302,121, Sep. 7, 1994, abandoned, which is a continuation-in-part of Ser. No. 79,341, Jun. 18, 1993, abandoned.

[51] Int. Cl.⁶ .......................... G03B 11/04; G02B 21/22
[52] U.S. Cl. .......................... 359/510; 359/376; 359/377; 359/511
[58] Field of Search ......................... 359/510, 511, 359/513, 613, 892, 894, 895, 375–378, 436, 441, 442

[56] References Cited

U.S. PATENT DOCUMENTS

| | | | |
|---|---|---|---|
| 1,693,021 | 11/1928 | Cameron | 359/613 |
| 2,285,658 | 6/1942 | Hitchcock | 359/513 |
| 2,583,228 | 1/1952 | Numbers | 359/511 |
| 3,512,860 | 5/1970 | Hansen et al. | 359/377 |
| 4,266,663 | 5/1981 | Geraci | 359/510 |
| 5,311,358 | 5/1994 | Pederson et al. | 359/510 |

*Primary Examiner*—James Phan
*Attorney, Agent, or Firm*—Hopgood, Calimafde, Kalil & Judlowe

[57] ABSTRACT

A surgical drape construction wherein a tubular body, peripherally assembled to a local lens aperture in a drape, is adapted for removable concentric engagement to the exposed end of the objective-lens barrel of a microscope, wherein the tubular body mounts a flat optically transparent element which closes the body, and wherein the flat transparent element is fixedly so inclined that a geometric normal to the flat transparent element is at an acute angle to the axis of concentric engagement. Would-be reflections are thereby deflected off-axis, and microscope viewing is materially enhanced for all subject-matter aspects with respect to incident light.

14 Claims, 1 Drawing Sheet

SURGICAL DRAPE FOR AN OPERATION MICROSCOPE

RELATED CASE

This application is a continuation-in-part of U.S. patent application Ser. No. 08/302,121, filed Sep. 7, 1994, (now abandoned) which is a continuation-in-part of original application, Ser. No. 08/079,341, filed Jun. 18, 1993 (now abandoned).

BACKGROUND OF THE INVENTION

The invention relates to a protective surgical drape construction for an operation microscope wherein an optically clear protective window is provided for the objective lens of the microscope.

Objective-lens protection has been a feature of protective surgical drapes for operation microscopes. Generally, such constructions take the form of a flanged annular body wherein the flange is sealed to the border of a local circular opening in the drape material and wherein the annular body is adapted for telescoping removable attachment to the objective-lens barrel or mount of the microscope. The annular body is axially short and provides mounting for a flat lens-protecting optically transparent element, which may be of glass or a suitable plastic, mounted perpendicular to the optical axis of the objective. Modern surgical microscopes of the character indicated incorporate sophisticated mountings with six dimensions of manipulated orientation of the objective, namely, three orthogonal axes of rotatable adjustment, and three orthogonal axes of rectilineal displacement, and for certain situations of adjusted orientation in relation to relatively fixed illumination, internal reflection between the objective lens and the flat protective transparent element can be a source of degraded viewing through the microscope.

BRIEF STATEMENT OF THE INVENTION

It is an object of the invention to provide an improved surgical drape of the character indicated.

A specific object is to meet the above object with a construction which inherently reduces the chances of degraded viewing through a drape-protected binocular microscope having stereoscopic-viewing capability.

Another specific object is to meet the above objects for the case of a microscope having provision for an internal source of projected field illumination.

A general object is to meet the above objects with a simple construction minimally affecting manufacturing cost, and requiring little or no additional skills for operational use.

The invention in a preferred embodiment meets these objects in a surgical drape construction wherein a tubular body, peripherally sealed to a local lens aperture in a drape, is adapted for removable concentric engagement to the exposed end of the objective-lens barrel of a microscope having spaced oculars for stereoscopic viewing through a single objective lens, wherein the tubular body mounts a flat optically transparent element which closes the body, and wherein the flat transparent element is fixedly so inclined that a geometric normal to the flat transparent element is at an acute angle to the axis of concentric engagement, i.e., to the optical axis of the objective lens. Would-be reflections are thereby deflected off-axis essentially in the same direction, for each of the viewing axes via the objective lens, and microscope viewing is materially enhanced for all subject-matter aspects with respect to the incident light.

BRIEF DESCRIPTION OF THE DRAWINGS

The invention will be described in detail for several embodiments, all in conjunction with the accompanying drawings, in which.

DETAILED DESCRIPTION

Figure 1:
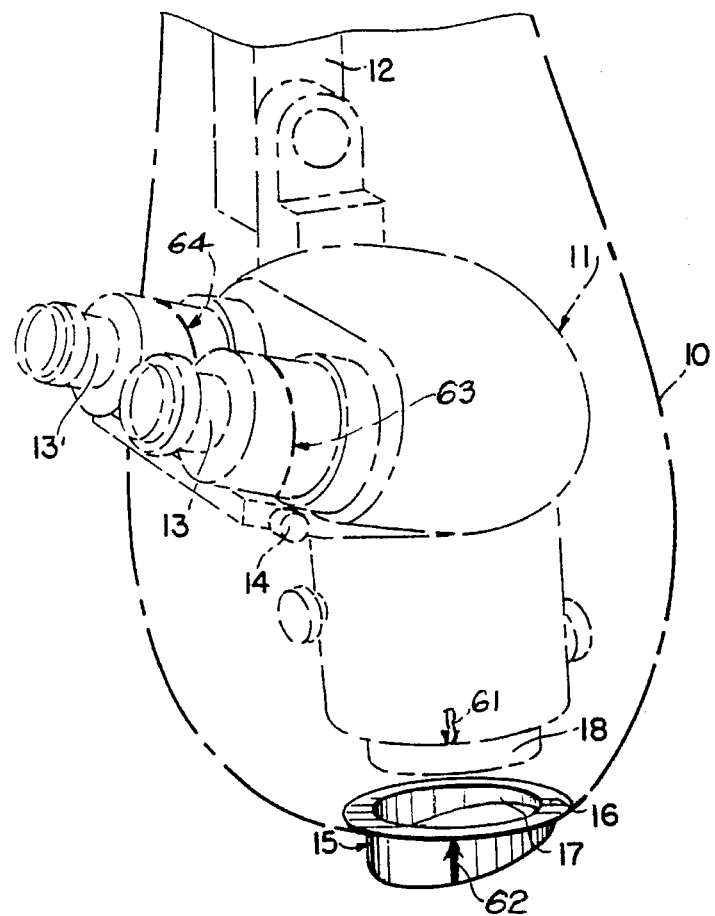
FIG. 1 is a simplified view in perspective of the viewing head of an operation microscope having stereoscopic viewing capability, the same being schematically shown in the course of assembly with a protective surgical drape of the invention.
Figure 2:
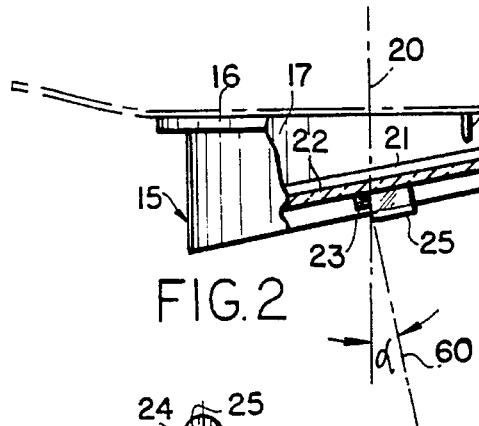
FIG. 2 is an enlarged view in side elevation of a local objective-lens fitment feature of the drape of FIG. 1, parts being broken-away and in longitudinal section.
Figure 3:
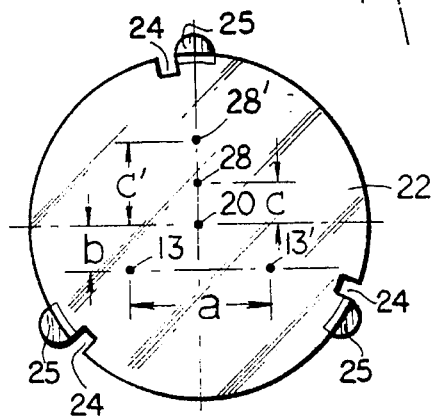
FIG. 3 is a plan view of an optically clear protective element of the drape fitting of FIG. 2, with illustrative schematic indication of various axis intercepts with this flat element.

Referring initially to FIGS. 1 to 3, the invention is shown generally by a protective drape 10 for shielding protection of an operation microscope, shown as a microscope head 11 with upper supporting structure which may include a floor stand, or a wall or ceiling suspension (not shown) and various articulating and displaceable elements that culminate in a support bracket 12. The microscope 11 is shown to include binocular-viewing oculars 13, 13' for stereoscopic viewing, with means 14 for selectively accommodating ocular spacing to user convenience.

The oculars 13, 13' are respectively associated with separate viewing axes which establish a geometric plane of viewing passage through a single objective lens having a lens barrel 18 concentric with the central axis 20 of the objective lens. In FIG. 2, this geometric plane is also indicated by the line 20.

The drape 10 includes a fitment 15 of the invention, having a radially outward flange 16 in peripherally sealed relation to the margin of a viewing opening in the material of the drape; and the bore 17 of fitment 15 is sized for concentric telescopic assembly to and removal from the exposed end of the barrel 18 of the single objective lens of microscope 11.

The fitment 15 is seen in FIG. 2 to be an annular molded-plastic part which has a cylindrical body wherein the bore 17 has one or more angularly spaced longitudinal ribs 19 for frictionally stressed retention to the lens barrel 18, concentric assembly being schematically suggested by designation in FIG. 2 of the central axis 20 of the objective lens of the microscope. The cylindrical body is truncated at an inclination which conforms to the slope of an annular seat or shoulder formation 21 in the bore 17. This shoulder formation 21 is adapted for removably seated positioning of a flat optically transparent element 22 which in FIG. 3 is seen to be circular. Coacting lug (23) and slot (24) formations at equal angular spacings enable bayonet-locking engagement and retention of transparent element 22 to its seating shoulder 21, upon axial registry of lugs 23 with slots 24, followed by incremental rotation out of such registry, as by finger-torquing of one or another of exposed lugs 25 which are integral formations of transparent element 22. The torqued rotary displacement of element 22 to the location at which lugs 25 abut lugs 23 (as seen in FIG. 2) will determine the angular location at which lugs 23 register with slots 24, namely, the angular location at which axial reception and removal of element 22 is possible, as when, in the course of a surgical operation, blood or other debris may clutter an optically used area of element 22; such a situation is rapidly resolved by removal of the thus-soiled element 22 and its replacement by a clean duplicate element 22.

FIG. 3 is additionally useful for a discussion of various axis intercepts (and thus axial spacings) at passage through or reflection from the flat optically transparent element 22. The ocular-viewing axis intercepts 13, 13' are shown at spacing a in a geometric plane of objective lens passage which may contain the central axis 20 of the objective lens, but which in FIG. 3 is shown at short offset b from axis 20. The microscope of FIG. 1 will be understood to be equipped with an internal source of field illumination wherein illumination is externally projected on an axis 28 which in FIG. 3 is shown with intercept at transparent element 22, the intercept of axis 28 being at opposite offset (c) from the central objective lens axis 20. Adjustable means will be understood to be part of the microscope whereby the offset (c) of the projection axis 28 for field illumination may be selected for optimal field illumination and viewing; preferably, although not necessarily, such adjustability is with symmetry in respect of the spaced viewing axes of oculars 13, 13', and a greater adjusted offset c' is shown at 28' for the axis of externally projected illumination.

Figure 4:
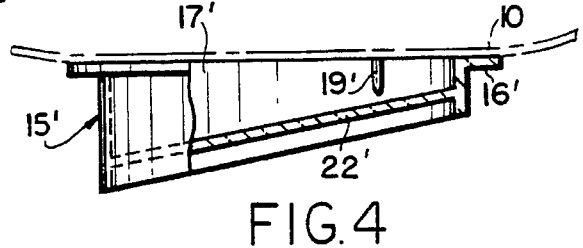
FIG. 4 is a view similar to FIG. 2, for a first modification.

FIG. 4 illustrates extreme simplicity of the invention in an embodiment in which the entire fitment 15' is the product of a single molding (e.g., injection-molding) operation, using a single plastic material, such as methylmethacrilate, which will provide a flat optically clear element 22' that is integrally united to the bore 17' and at an inclination which is consistent with the truncation. The sealed assembly of flange 16' to an aperture in drape 10, and friction-rib (19') engagement to the objective-lens barrel 18, are as described for the embodiment of FIGS. 2 and 3.

Figure 5:
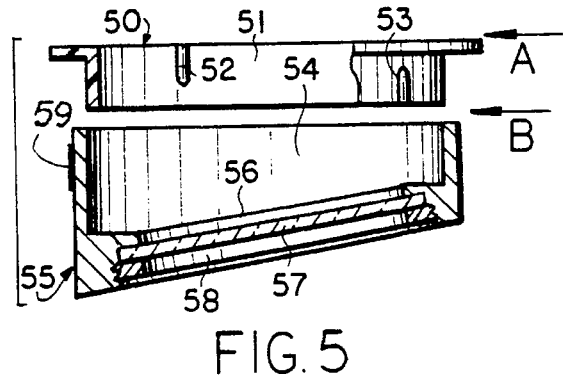
FIG. 5 is an exploded view, otherwise similar to Figs. 2 and 4, for a second modification.

In the embodiment of FIG. 5, a simple flanged annular body 50, with a cylindrical bore 51 and one or more friction ribs 52, lends itself to flange-bonding to the rim of a circular viewing opening in the material of drape 10 (not shown in FIG. 5, but suggested schematically by an upper arrow A). The body 50 is shown with one or more external friction ribs 53 for retention of a telescopic fit of body 50 to the cylindrical bore 54 of a second (and reusable) part 55 of the embodiment of FIG. 5. When part 50 is preassembled and sealed to drape 10, as suggested at A, part 50 may be of molded plastic and discarded with the drape, after single-patient use. On the other hand, part 55 is not necessarily to be discarded and may be autoclavable, thus of precision-molded or machined stainless-steel construction. More particularly, the part 55 is shown to be formed with an annular shoulder 56 for oriented peripheral support of a flat glass element 57, preferably of optical quality, and this support is retained by a ring member 58 in threaded engagement with a counterbore that is concentric with shoulder 56.

In an alternative employment of structure described in connection with FIG. 5, the flange of body 50 is not bonded in preassembly to the drape material. Instead, the viewing aperture of the drape will be understood to have a coated annulus of pressure-sensitive adhesive, concentric with the opening and designed for registry with the flange of body 50, whether applied to the upper level suggested at A or pulled over the cylindrical remainder of body 50, as suggested by introduction at a lower level B, with adhesive coating facing the underside of the flange of body 50. Thereafter, upon telescopically assembling part 55 to part 50, to the point of adjacency to the flange of body 50, the assembly and peripherally sealed relation to the drape are assured.

It will be seen that the described embodiments of the invention meet stated objects and offer different features of convenience and utility for various operation usages of microscope 11. In all cases, the flat optically transparent plate is inclined to the optical axis of the objective lens of the microscope. This inclination may be stated to be an acute-angle relationship $\alpha$ between a normal 60 to the flat transparent member, with respect to the objective-lens axis 20, where the acute angle $\alpha$ is suitably in the range 10° to 30°, and is preferably about 15°.

Stated in other words, for the preferred embodiment wherein the two spaced oculars 13, 13' achieve stereoscopic viewing, via separate spaced viewing axes through the single objective lens, a geometric plane of viewing passage through the objective lens is established by the respective ocular-viewing axes. This geometric plane may include, or be at one direction of offset from, the central optical axis of the objective lens. The plane of transparent element 22 may thus be viewed as having been tilted about an axis which is either substantially normal to, or is otherwise in a second geometric plane that is substantially normal to, the central axis 20 of the objective lens. And the tilt angle $\alpha$ is particularly useful in enabling transparent element 22 to deflect internal reflection of projected illumination (e.g., at axis intercepts 28 or 28') away from degrading influence on the quality of microscope viewing, while also performing a similar function for extraneous light sources externally to the microscope.

This preferred orientation of the transparent element 22 can be ensured by providing a marker 62 on the fitting 15 and by providing a corresponding marker 61 on the microscope 11 on or near the lens barrel as shown in FIG. 1. When these markers 61 and 62 register, the transparent element 22 is in its advantageous orientation.

As can be further seen in FIG. 1 the two spaced oculars 13 and 13' for stereoscopic viewing already impose a certain orientation of the drape 10 because the drape 10 has to accommodate the two oculars 13 and 13', as is schematically depicted by line segments 63 and 64. Because the fitting is preferably a preassembled part of the drape 10, this circumstance automatically leads to a pre-orientation of the transparent element 22, wherein the pre-orientation is at least an approximation of the preferred orientation.

In an especially advantageous orientation of the transparent element 22, the geometric normal to the flat transparent element 22 is parallel to or lies in a plane defined by the central axis 20 of the objective lens and by the illumination axes, whose intercept 28 with the flat transparent element 22 can be seen in FIG. 3. This very special orientation of the flat transparent element 22, or 57, in the case of the embodiment of FIG. 5, ensures that reflections from the field illumination are not biased toward a single one of the ocular viewing axes because, with this special orientation, the inclination of the flat transparent element 22 is symmetrical to both ocular-viewing axes, as viewed from the illumination axis.

With respect to the embodiment of FIG. 5, it is observed that the part 55 having the transparent plate 57 enables assembly of plate 57 to the body 50 at any selected angle of rotation about the central axis of the objective lens, whereby to set the angle $\alpha$ for minimum cross-light exposure to an ambient source which might otherwise affect the clarity of microscope viewing. And having thus selected the angle of rotation about the central axis of the objective lens, the selected angle serves both of the ocular-viewing axes with substantially equal effectiveness. There may of course be a marker 59 cooperating with marker 61 on the microscope 11 and corresponding to a desired preselected angle of rotation.

The embodiments of FIGS. 2 and 5 are recognizably useful for microscope applications wherein laser radiation utilizes microscope optics, the transparent elements 22, 57 being removable for such usage.

From the foregoing description and the drawings, the invention will be seen to provide drape structure which has the inherent capability of correctly orienting the transparent element 22 with respect to the ocular-viewing axes and the illumination axis of projected field illumination, all for the case of a stereopticaly binocular viewing system having convergent viewing axes through a single objective lens, wherein one end of the barrel of the objective lens is externally exposed. The viewing axes establish a first geometric plane through said objective lens, and the illumination axis and the central axis of the objective lens establish a second geometric plane through the objective lens wherein the second geometric plane is perpendicular to the first geometric plane and bisects the convergence of the viewing axes. The drape is an elongate bag-like protective device forming an envelope of pliant plastic material which has an upper open end adapted to receive the microscope and which is adapted to be closed for completion of bag-enclosure of the microscope, and the drape having a formed localized lower region of the lens-barrel engageability. The formed lower region comprises a tubular body peripherally assembled to the pliant plastic material at a local lower-end opening in the envelope, and the tubular body has a flat optically transparent element peripherally closing the tubular body. The flat optically transparent element is acutely inclined to the viewing and illumination axes at passage of these axes through the optically transparent material. The envelope has a lateral-side opening facing in one direction of offset away from the elongate direction of the envelope and is removably adapted for protective closure of said lateral-side opening around the viewing oculars. The direction of acute-angle inclination of the flat optically transparent element is symmetrical with respect to the said direction of offset of the lateral-side opening, whereby upon assembly of the drape to the microscope, the inclination of the flat optically transparent element substantially symmetrically accommodates the viewing axes to the illumination axis. For greater precision, a local angular indicium mark on the lens barrel is in angular register with a local angular indicium mark on the tubular body when the inclination of the flat optically transparent element precisely symmetrically accommodates the viewing axes to the illumination axis.

What is claimed is:

1. In combination, a stereoscopic operation microscope having an internal source of projected field illumination on an illumination axis and having viewing oculars on spaced viewing axes that are convergent via a single objective lens having a central axis, the viewing oculars projecting locally from one lateral side of the microscope and at offset from said central axis, said objective lens having a barrel one end of which is externally exposed, said viewing axes establishing a first geometric plane through said objective lens, and said illumination axis and said central axis establishing a second geometric plane through said objective lens wherein said second geometric plane is perpendicular to said first geometric plane and bisects the convergence of said viewing axes; and a protective drape comprising an upstanding envelope of pliant plastic material having a formed lower localized region of lens-barrel engageability and an upper lateral-side opening of viewing-ocular engageability, wherein said lateral-side opening faces in one direction of offset away from the elongate direction of said envelope, for selective protective closure of the lateral-side opening around the viewing oculars; said formed lower region comprising a tubular body peripherally assembled to the pliant plastic material at a local lower opening in said envelope, said tubular body having a flat optically transparent element peripherally closing said body, and said flat optically transparent element being acutely inclined to said viewing and illumination axes at passage of said axes through said optically transparent material, said one direction of offset being so related to the inclination of said flat optically transparent element that when said envelope is fitted to the microscope with the lateral-side opening protectively engaged around the viewing oculars, the inclination of said flat optically transparent element symmetrically accommodates the viewing axes to the illumination axis.

2. The combination of claim 1, in which said acute angle is in the range of 10° to 30° from a plane that is normal to said central axis.

3. The combination of claim 2, in which said acute angle is in the range of 15° to 20° from a plane that is normal to said central axis.

4. In combination, a stereoscopic operation microscope having an internal source of projected field illumination on an illumination axis and having viewing oculars on spaced viewing axes that are convergent via a single objective lens having a central axis, wherein one end of a barrel for said lens is externally exposed, said viewing axes establishing a first geometric viewing plane through said objective lens, and said illumination axis and said central axis establishing a second geometric plane through said objective lens wherein said second geometric plane is perpendicular to said first geometric plane and bisects the convergence of said viewing axes; a tubular body detachably securable to said lens barrel and supporting a flat optically transparent element peripherally closing said tubular body, said flat optically transparent element being acutely inclined to said viewing and illumination axes at passage of said axes through said optically transparent element; and a local angular indicium mark on the lens barrel in angular register with a local angular indicium mark on said tubular body when the inclination of said flat optically transparent element precisely symmetrically accommodates the viewing axes to the illumination axis.

5. The combination of claim 4, in which a surgical drape of pliant material has an opening that is adapted for sealing engagement around said tubular body and for sealing engagement around the region of ocular viewing and otherwise to envelope said microscope.

6. In combination, a stereoscopic operation microscope having an internal source of projected field illumination on an illumination axis and having viewing oculars on spaced viewing axes that are convergent via a single objective lens having a central axis, wherein one end of a barrel for said lens is externally exposed, said viewing axes establishing a first geometric plane through said objective lens, and said illumination axis and said central axis establishing a second geometric plane through said objective lens wherein said second geometric plane is perpendicular to said first geometric plane and bisects the convergence of said viewing axes: an elongate bag-like protective drape forming an envelope of pliant plastic material having an upper open end adapted to receive the microscope and to be closed for completion of bag-enclosure of the microscope, said drape having a formed localized lower region of lens-barrel engageability; said formed region comprising a tubular body peripherally assembled to the pliant plastic material at a local lower-end opening in the envelope, said tubular body having a flat optically transparent element peripherally closing said tubular body, said flat optically transparent element being acutely inclined to said viewing and illumination axes at passage of said axes through said optically transparent material; said envelope having a lateral-side opening facing in one direction of offset away from the elongate direction of said envelope and removably adapted for protective closure of said lateral-side opening around the viewing oculars; the direction of acute-angle inclination of said flat optically transparent element being symmetrical with respect to the said direction of offset of said lateral-side opening, whereby upon assembly of said drape to the microscope, the inclination of said flat optically transparent element substantially symmetrically accommodates the viewing axes to the illumination axis; and a local angular indicium mark on the lens barrel in angular register with a local angular indicium mark on said tubular body when the inclination of said flat optically transparent element precisely symmetrically accommodates the viewing axes to the illumination axis.

7. The combination of claim 6, in which said tubular body has a peripherally continuous radially outward flange in peripherally assembled relation to the pliant plastic material.

8. The combination of claim 6, in which said tubular body and said optically transparent element are the integrally united product of a single molding operation with an optically transparent plastic material.

9. The combination of claim 6, in which said tubular body includes an internal annular shoulder establishing a single plane of seating reference for said flat optically transparent element.

10. The combination of claim 6, in which said tubular body and said optically transparent element have coacting formations for removable bayonet engagement and oriented assembly of said transparent element to said tubular body.

11. The combination of claim 10, in which said flat optically transparent element is a circular plate having angularly spaced radially outward lugs with bayonet-retainable engagement to angularly spaced axially projecting lug formations of said tubular body.

12. The combination of claim 6, in which said optically transparent element is of glass.

13. The combination of claim 6, in which said optically transparent element is of a transparent plastic material.

14. The combination of claim 6, in which said tubular body is cylindrical and formed with a peripherally continuous radially outward flange in peripherally sealed relation to said pliant plastic material, and in which said optically transparent element has its own separate tubular mount sized for telescoping removable engagement to said tubular body, the inclination of said optically transparent element being fixedly established in and by said separate tubular mount.

* * * * *